(12) United States Patent
Schiffer (10) Patent No.: US 12,303,711 B2
(45) Date of Patent: May 20, 2025

(54) ENHANCED TREATMENT OF BRAIN DISORDERS UTILIZING COORDINATED NEGATIVE SUPPRESSIVE STIMULATION AND RELATED DEVICES DESIGNED TO ACHIEVE TREATMENT

(71) Applicant: Fredric Schiffer, Newton Highland, MA (US)

(72) Inventor: Fredric Schiffer, Newton Highland, MA (US)

( * ) Notice: Subject to any disclaimer, the term of this patent is extended or adjusted under 35 U.S.C. 154(b) by 0 days.

(21) Appl. No.: 18/948,675

(22) Filed: Nov. 15, 2024

(65) Prior Publication Data

US 2025/0073490 A1 Mar. 6, 2025

Related U.S. Application Data

(62) Division of application No. 17/393,074, filed on Aug. 3, 2021, now Pat. No. 12,194,310.

(60) Provisional application No. 63/060,177, filed on Aug. 3, 2020.

(51) Int. Cl.
*A61N 5/00* (2006.01)
*A61M 21/02* (2006.01)
*A61N 5/06* (2006.01)
*A61M 21/00* (2006.01)

(52) U.S. Cl.
CPC .......... *A61N 5/0618* (2013.01); *A61M 21/02* (2013.01); *A61M 2021/0027* (2013.01); *A61M 2021/0066* (2013.01); *A61M 2210/0662* (2013.01); *A61N 2005/005* (2013.01); *A61N 2005/0626* (2013.01); *A61N 2005/0651* (2013.01); *A61N 2005/0652* (2013.01)

(58) Field of Classification Search
None
See application file for complete search history.

(56) References Cited

U.S. PATENT DOCUMENTS

| 8,517,911 B1 | 8/2013 | Thompson |
| 2002/0198577 A1 | 12/2002 | Jaillet |
| 2011/0040356 A1* | 2/2011 | Schiffer ............... A61M 21/02 |
| | | 607/88 |

(Continued)

OTHER PUBLICATIONS

Dumont L, Larochelle-Brunet F, Theoret H, Riedl R, Sénécal S, Léger P-M (2018) Non-invasive brain stimulation in information systems research: A proof-of-concept study. PLoS ONE 13(7): e0201128. https://doi.org/10.1371/journal.pone.0201128.

*Primary Examiner* — Sana Sahand
(74) *Attorney, Agent, or Firm* — JWIP & Patent Services, LLC; Jacob G. Weintraub, Esq.

(57) ABSTRACT

The present invention is directed to enhanced methods of treating brain disorders, and devices suitable to implement these methods. In particular, the methods of treatment and related devices of the present invention utilize the coordinated application of negative suppressive stimulation of the brain hemisphere with the more negative valence in combination with transcranially applied light energy to the lateral forehead to activate the underlying cortex of the brain hemisphere with the more positive valence, e.g., synergistically. In addition, such methods and devices may be suitable to address co-morbid brain disorders (e.g., psychiatric disorder co-morbid with depression) in a more effective manner.

10 Claims, 2 Drawing Sheets

(56) References Cited

U.S. PATENT DOCUMENTS

2012/0010685 A1   1/2012   Streeter et al.
2013/0211183 A1   8/2013   Schiffer

* cited by examiner

ENHANCED TREATMENT OF BRAIN DISORDERS UTILIZING COORDINATED NEGATIVE SUPPRESSIVE STIMULATION AND RELATED DEVICES DESIGNED TO ACHIEVE TREATMENT

RELATED APPLICATIONS

This application claims priority to U.S. Utility patent application Ser. No. 17/393,074, filed on Aug. 3, 2021; which claims priority to U.S. Provisional Patent Application No. 63/060,177, filed on Aug. 3, 2020; the entirety of each of which is incorporated herein by reference.

BACKGROUND OF THE INVENTION

Hundreds of millions of people world-wide suffer from brain disorders. Such disorders include psychiatric and neurologic disorders including, but not limited to disorders such as, depression, attention deficit disorder, schizophrenia, bipolar disorder, anxiety disorders, alcoholism, eating disorders such as anorexia and bulimia, phobias, Asperser's syndrome, dissociative disorders, insomnia, Alzheimer's Disease, Parkinson's Disease, Autism, Stroke, and borderline personality disorder. These disorders are often chronic and require long-term treatment/therapy options that provide varying degrees of successful outcomes Anxiety disorders are the most prevalent illness in the United States with a prevalence of over 40 million adults, or about 18% of the population, each year. Anxiety disorders are often associated with depression, with persons suffering it being six times more likely to have a psychiatric hospitalization. Moreover, depression is the leading cause of disability world-wide, with an overall prevalence of almost 30% of populations studied having some sub-population having an incidence of over 50%. Sadly, depression not only causes profound suffering for the individual and their family, but also reduces social functioning and productivity and promotes other serious diseases, including diseases from cardiovascular to Alzheimer's Diseases, and is strongly associated with substance abuse and other mental illnesses as well as suicide. Moreover, drug abusing patients demonstrate mental distress, health complications, loss of productivity, and increased criminality, which are injurious not only to patients and their families, but also to society as a whole.

Furthermore, anxiety, depression, substance abuse, and post-traumatic stress disorders are often co-morbid, with the ultimate effect resulting in the need for reliable treatments that might account for all of these disorders simultaneously. Although treatment options exist (often addressing individual disorders alone), given the prevalence and often the life-long concerns of these disorders, new and advancing treatment options are highly desirable.

As such, new and improved methods of treating brain disorders are needed, along with new devices that are capable of implementing these methods. In particular, there is a need for treatments that might address the noted co-morbid disorders in a more effective manner.

SUMMARY OF THE INVENTION

Accordingly, the present invention is directed to enhanced methods of treating brain disorders, and devices suitable to implement these methods. In particular, the methods of treatment and related devices of the present invention utilize the coordinated application of negative suppressive stimulation of the brain hemisphere with the more negative valence in combination with transcranially applied light energy to the lateral forehead to activate the underlying cortex of the brain hemisphere with the more positive valence, e.g., synergistically. In addition, such methods and devices may be suitable to address co-morbid brain disorders (e.g., psychiatric disorder co-morbid with depression) in a more effective manner.

As such, one aspect of the present invention provides a method for enhanced treatment of a brain disorder characterized by neurologic or psychiatric disorder symptomology with a lateralized difference in hemispheric emotional valence, utilizing coordinated negative suppressive stimulation, comprising: identifying a patient with a brain disorder; measuring a left hemispheric emotional valence for a left hemisphere of a brain of the patient and a right hemispheric emotional valence for a right hemisphere of the brain of the patient to identify a patient with a lateralized difference in hemispheric emotional valence; determining which hemisphere of the brain of the patient with a lateralized difference in hemispheric emotional valence has a more positive valence, and which hemisphere of the brain has a more negative valence; transcranially applying light energy having a wavelength of between 300 nm to 1500 nm and a power density at the scalp of up to 10 W/cm$^2$ to the brain of said patient with the brain disorder with lateralized difference in hemispheric emotional valence, wherein the light energy is transcranially applied to the lateral forehead to activate the underlying cortex of the brain hemisphere with a more positive valence for a defined period; and coordinated application of negative suppressive stimulation of the brain hemisphere with the more negative valence, such that the brain disorder with lateralized difference in hemispheric emotional valence is treated in said patient.

Another aspect of the present invention provides a device for the enhanced treatment of a brain disorder characterized by neurologic or psychiatric disorder symptomology with a lateralized difference in hemispheric emotional valence, utilizing coordinated negative suppressive stimulation, comprising a light emitting diode (LED) for transcranial application of light energy having a wavelength of between 300 nm to 1500 nm and a power density at the scalp of up to 10 W/cm$^2$ to the brain of a patient with a brain disorder characterized by neurologic or psychiatric disorder symptomology with a lateralized difference in hemispheric emotional valence, wherein the light emitting diode (LED) is suitable for asymmetric transcranial application to the forehead of the patient to activate the underlying cortex of the brain hemisphere with a more positive valence for a selectable (defined) period of time and is suitable to coordinate with the application of negative suppressive stimulation of the brain hemisphere with the more negative valence effected through the incorporation and use of one or more of the following components:

a calmative auditory stimulation component designed to deliver asymmetric localized calmative sound to the ear contralateral to the brain hemisphere with the more negative valence, or a pulsing light emitting diode (LED) for transcranial application of light energy capable of delivering light energy between 300 nm to 1500 nm and a power density at the scalp of up to 10 W/cm$^2$ to the brain of said patient as low frequency pulsating light energy ipsilateral to the brain hemisphere with the more negative valence, and wherein the negative suppressive stimulation is coordinated with the asymmetric transcranial application to the forehead of the patient to activate the underlying cortex of the brain hemisphere with the more positive valence.

BRIEF DESCRIPTION OF THE FIGURES

Advantages of the present methods and related devices will be apparent from the following detailed description, which description should be considered in combination with the accompanying figures, which are not intended to limit the scope of the invention in any way.

DETAILED DESCRIPTION OF THE INVENTION

A number of existing split-brain studies have suggested that most people are of two minds, each associated with one brain hemisphere. One hemisphere is associated with an immature mind that may be affected by childhood traumas and is prone to self-destructive thoughts and feelings leading to diagnosable symptoms. The other hemisphere is much more resilient to the past traumas and functions at a much higher level. The healthier hemisphere is the right hemisphere in about 50% of patients, and this runs counter to the established notion that negative emotions are always associated with the right hemisphere The present invention has identified the synergistic advantage of coordinating transcranial photobiomodulation to the positive hemisphere with negative suppressive stimulation of the negative hemisphere. As such, the present invention provides for methods of treatment of brain disorders, e.g., characterized by neurologic or psychiatric disorder symptomology, with a lateralized difference in hemispheric emotional valence (HEV), as well as related devices. In particular, the present invention utilizes the coordinated application of negative suppressive stimulation of the brain hemisphere with the more negative valence in combination with transcranially applied light energy to the lateral forehead to activate (e.g., applied to) the underlying cortex of the brain hemisphere with the more positive valence, e.g., synergistically. In this respect, a coordinated treatment of both hemispheres according to their HEV, activating the positive side while using suppressive stimulation of the negative side, improves the statistical and clinical outcomes in patients with brain disorders, e.g., a combined history of OUD, MD, AD, and PTSD.

The treatment of brain disorders using the methods and devices of the present invention comprises treating (e.g., reducing or eliminating) the symptomology of the psychiatric disorders or neurologic disorders, e.g., showing an enhancement of treatment over unilateral tPBM to the positive hemisphere.

The present invention, including devices and methods will be described with reference to the following definitions that, for convenience, are set forth below. Unless otherwise specified, the below terms used herein are defined as follows:

I. Definitions

As used herein, the term "a," "an," "the" and similar terms used in the context of the present invention (especially in the context of the claims) are to be construed to cover both the singular and plural unless otherwise indicated herein or clearly contradicted by the context.

The term "about" is used herein in reference to the degree or extent of the term which it modifies, and that such extent may be 100% or near to but not exactly 100% of the modified term; industry accepted standards will assist in defining the quantitative aspects of how "near" 100% is defined. In particular embodiments, the term "about" indicates ±2%, ±1% or ±0.5%. In a particular embodiment, for example, the language "about 2-4 Hz" would be exactly 2-4 Hz; and in an alternative particular embodiment, for example, the language "about 2-4 Hz" would mean 2-4 Hz±2%, 19%±1%, or 19%±0.5%.

The language "and/or" is used herein to mean both "and" in the conjunctive form and "or" in the disjunctive form.

The language "brain disorder" is art recognized and is used herein to describe a neurologic or a psychiatric disorder, i.e., characterized by symptomology of a neurologic or psychiatric disorder.

As used herein, the term "co-morbid" or "co-existent" refers to any psychiatric disorders that exist in addition to a primary disease or disorder, such as depression.

The term "coordinated" is used herein to describe the characteristic or action of bringing two or more different elements/steps of a complex activity, method, or device into a relationship that will ensure efficiency or harmony in a synergistic manner. In certain embodiments the coordinate element/step (e.g., application) would occur in a pre-defined time course in relation to another element/step, e.g., occurring simultaneously to another element/step.

As used herein, the terms "depression," "depressive disorder," "dysthymic disorder," "major depressive disorder" and "unipolar depression" refer to a DSM-IV definition of depression. In certain embodiments, depression may be defined as a combination of sadness, loss of energy, feelings of hopelessness, difficulty concentrating, insomnia, and irritability. The National Comorbidity Survey reported that 46% of men and 58% of women have suffered in their lifetime at least a two-week period in which they experienced a persistent depressed mood. Major depression has a lifetime prevalence of about 16%, and it is estimated that by 2020, it will be the second greatest contributor to the impairment of global health. A recent Australian survey reported that anxiety disorders were the most common mental disorder with a lifetime prevalence of 26%. Depression can run in families, and usually starts between the ages of 15 and 30. It is much more common in women. Women can also get postpartum depression after the birth of a baby. Some people get seasonal affective disorder in the winter. Depression is one part of bipolar disorder. Depression by any definition does not encompass most psychological disorders. For example, people who are diagnosed with schizophrenia have delusions and/or hallucinations and have a deterioration of their personality rendering them almost always incapable of complex work or sustained relationships. A person with an anxiety disorder will suffer excessive apprehension and worry with heightened arousal but will not feel sad or hopeless unless he/she suffers, in addition, a coexisting depressive disorder. A person who abuses substances will usually not also suffer anxiety or depression, although he may have a dual diagnosis in which both a substance abuse disorder and another disorder such as an anxiety disorder or a depressive disorder are also present. 47% of patients diagnosed with schizophrenia also have a substance abuse disorder.

Further, depression is associated with the integration of multiple intracellular signals that regulate neuronal response (i.e., changes in G protein, cyclic adenosine monophosphate, or protein kinase and the induction of gene transcription). These intracellular signals ultimately affect the expression of specific genes. It is these abnormalities of intracellular signal transduction and/or gene expression that underlie much of the physiology of depression. Other neurotransmitters (e.g., acetylcholine, gamma amino butyric acid, melatonin, glycine, histamine), hormones (e.g., thyroid and adrenal hormones), and neuropeptides (e.g., corticotropin-releasing hormone, endorphins, enkephalins, vasopressin, cholecystokinin, substance P) also play significant roles in the physiology of depression.

In depression, functional imaging studies most consistently demonstrate a decreased prefrontal cortex (PFC), especially left PFC, blood flow. These findings correlate with severity of illness and cognitive impairment. Functional imaging in depressed patients also show basal ganglia abnormalities, involving decreased blood flow and metabolism as well as increased activity of amygdala. In major depression, other neuroimaging studies show abnormalities in the hippocampus, cingulate, and related parts of the striatum and thalamus. Together, data offer a neural model for depression in which dysfunction of limbic, striatal, and PFC structures impair the modulation of the amygdala/hippocampus complex and lead to abnormal processing of emotional stimuli. Depression also tends to be associated with lesions in the left frontotemporal or right parieto-occipital regions.

The term "enhanced" is used herein to describe the relatively improvement of treatment over an existing standard treatment. For example, the methods of the present invention are enhanced, showing improvement over unilateral tPBM to the positive hemisphere of the brain.

The language "hemispheric emotional valence (HEV)" is art-recognized, for example, as described in the first two references cited in the "References" section.

The language "negative suppressive stimulation" is used herein is suppressive stimulation to the hemisphere with the more negative hemispheric valence. This is coordinated with an active stimulation of a hemisphere with a more positive hemispheric emotional valence.

The language "neurologic disorder" is art-recognized and is used herein to describe diseases of the central and peripheral nervous system, e.g., the brain, spinal cord, cranial nerves, peripheral nerves, nerve roots, autonomic nervous system, neuromuscular junction, and muscles. These disorders include epilepsy, Alzheimer disease and other dementias, cerebrovascular diseases including stroke, migraine and other headache disorders, multiple sclerosis, Parkinson's disease, neurological infections, brain tumors, traumatic disorders of the nervous system due to head trauma, and neurological disorders as a result of malnutrition As used herein, the term "psychiatric disorders" refers to any psychiatric disorders including, but not limited to, depression, attention deficit disorder, schizophrenia, bipolar disorder, anxiety disorders, alcoholism, eating disorders such as anorexia and bulimia, phobias, Asperser's syndrome, dissociative disorders, insomnia, and borderline personality disorder. The ICD-10 diagnostic system, like the earlier DSM-IV, applies to these psychiatric disorders. Psychiatric disorders also include substance abuse disorders (i.e., alcohol abuse or opiate dependence or abuse) caused either by depression or not caused by depression, persistent anxiety, anxiety attacks, feelings of panic, fears of social contacts, nightmares, flashbacks, obsessive thoughts, compulsive behavior, attention disorder, sexual problem, and irrational thinking.

The term "remission" is art-recognized and is used herein to describe the state of absence of disease activity in patients with a chronic illness. Remission is measured using a rating scale, e.g., where a score of greater than fifteen on the rating scale correlates to having an anxiety disorder and a score of ten or less on the rating scale correlates to being in remission and no longer manifesting an abnormal level of anxiety.

As used herein, the terms "subject", and "patient" are used interchangeably. The terms "subject" and "patient" refer to a human person that is capable of suffering from a brain disorder.

As used herein, the term "transcranial" refers to a procedure that is performed through the cranium, or the skull that covers and protects the brain. Transcranial refers to a non-invasive method that delivers energy to the neurons of the brain. Transcranial therapy can cause activity in specific or general parts of the brain with minimal discomfort, allowing the functioning and interconnections of the brain to be studied and/or treated. The light device is held on the scalp, no actual contact is necessary, and the energy passes through the skull and into the brain. Small induced currents can then make brain areas below the light device more or less active, depending on the settings used.

The language "transcranial photobiomodulation" or "tPBM" is art-recognized and is used to describe the application of light energy to the brain to affect the brain, including the application of low-level laser and/or LED light.

As used herein, and unless otherwise specified, the terms "treat," "treating" and "treatment" refer to the eradication/remission or amelioration of a disease, disorder, or condition, or of one or more symptoms associated with the disease, disorder or condition as evidenced through symptomology or underlying physiological mechanistics related to the disorder. In certain embodiments, the term "treating" describes enhancing a person's positive outlook or suppressing a person's negative outlook, e.g., this may refer to a person's psychological well-being, including but not limited to their emotional, cognitive, and motivational states, where those persons who are successfully treated can find more appreciation for life, for themselves (improved self-esteem), their work, and their personal relationships. In certain embodiments, the terms describe minimizing the advancement or worsening of the disease, disorder, or condition resulting from the administration of the methods or devices of the present invention to a patient with such a disease, disorder, or condition. In some embodiments, the terms refer to the administration of a method or device provided herein, after the onset of symptoms of the particular disease, disorder, or condition. The terms "treating", "treatment", or the like, as used herein covers the treatment of a disease, disorder, or condition in a subject, and includes at least one of: (i) inhibiting the disease, disorder, or condition, i.e., partially or completely halting its progression; (ii) relieving the disease, disorder, or condition, i.e. causing regression of symptoms of the disease, disorder, or condition, or ameliorating a symptom of the disease, disorder, or condition; and (iii) reversal or regression of the disease, disorder, or condition, for example, eliminating or curing of the disease, disorder, or condition.

The language, "well-being" is used to describe a state of wellness of body, mind and soul, where all are in a state of health, the individual is happy and prospering. Well-being describes the overall welfare of an individual including a good or satisfactory condition of existence. Well-being is a state characterized by health, happiness, and prosperity.

In psychiatry, ICD-10, and the "Diagnostic and Statistical Manual of Mental Disorders, 4th Edition (DSM-IV)" are manuals published by the World Health Organization and American Psychiatric Association (APA), respectively, that includes all currently recognized mental health disorders. However, ICD-10 is now the official standard, and in ICD-10 there are two diagnoses for depression, Major Depression and Dysthymic Disorder, as described below. Each of the diagnostic entities in the ICD-10 are supported not only by clinical descriptions, but also by biological studies that use electroencephalography (EEG), magnetoencephalography (MEG), functional magnetic resonance imaging (fMRI), evoked potentials, electrodermal activity, biochemical markers (catecholamines and catecholamine metabolites; indoleamines and indoleamine metabolites, acetylcholine, histamine, aminoacids, melatonin, prostaglandins, opoid peptides, neuropeptides, enzymes, receptor densities), psychoimmunological markers, genetic markers, and animal models.

The language "Major Depressive Disorder" is characterized by one or more Major Depressive Episodes (i.e., at least 2 weeks of depressed mood or loss of interest accompanied by at least four additional symptoms of depression). Dysthymic Disorder is characterized by at least 2 years of depressed mood for more days than not, accompanied by additional depressive symptoms that do not meet criteria for a Major Depressive Episode.

Criteria for Major Depressive Episode include:
A. Five (or more) of the following symptoms have been present during the same 2-week period and represent a change from previous functioning; at least one of the symptoms is either (1) depressed mood or (2) loss of interest or pleasure. Note: Do not include symptoms that are clearly due to a general medical condition, or mood-incongruent delusions or hallucinations.
 (1) depressed mood most of the day, nearly every day, as indicated by either subjective report (e.g., feels sad or empty) or observation made by others (e.g., appears tearful). Note: In children and adolescents, can be irritable mood.
 (2) markedly diminished interest or pleasure in all, or almost all, activities most of the day, nearly every day (as indicated by either subjective account or observation made by others)
 (3) significant weight loss when not dieting or weight gain (e.g., a change of more than 5% of body weight in a month) or decrease or increase in appetite nearly every day. Note: In children, consider failure to make expected weight gains.
 (4) insomnia or hypersomnia nearly every day
 (5) psychomotor agitation or retardation nearly every day (observable by others, not merely subjective feelings of restlessness or being slowed down)
 (6) fatigue or loss of energy nearly every day
 (7) feelings of worthlessness or excessive or inappropriate guilt (which may be delusional) nearly every day (not merely self-reproach or guilt about being sick)
 (8) diminished ability to think or concentrate, or indecisiveness, nearly every day (either by subjective account or as observed by others)
 (9) recurrent thoughts of death (not just fear of dying), recurrent suicidal ideation without a specific plan, or a suicide attempt or a specific plan for committing suicide
B. The symptoms do not meet criteria for a Mixed Episode.
C. The symptoms cause clinically significant distress or impairment in social, occupational, or other important areas of functioning.
D. The symptoms are not due to the direct physiological effects of a substance (e.g., a drug of abuse, a medication) or a general medical condition (e.g., hypothyroidism).
E. The symptoms are not better accounted for by Bereavement, i.e., after the loss of a loved one, the symptoms persist for longer than 2 months or are characterized by marked functional impairment, morbid preoccupation with worthlessness, suicidal ideation, psychotic symptoms, or psychomotor retardation.

Diagnostic criteria or Dysthymic Disorder include:
A. Depressed mood for most of the day, for more days than not, as indicated either by subjective account or observation by others, for at least 2 years. Note: In children and adolescents, mood can be irritable, and duration must be at least 1 year.
B. Presence, while depressed, of two (or more) of the following:
 (1) poor appetite or overeating
 (2) insomnia or hypersomnia
 (3) low energy or fatigue
 (4) low self-esteem
 (5) poor concentration or difficulty making decisions
 (6) feelings of hopelessness The DSM-IV (1), the International Classification of Diseases (ICD-10-CM) (2), and as described in The Comprehensive Textbook of Psychiatry (3), thus, define depressive disorders, which in the ICD-10-CM are given specific diagnostic codes: major depression is F33 and dysthymia is F34.1. In distinction from the depressive disorders, the DSM-IV, ICD-10-CM, the Comprehensive Textbook of Psychiatry, and the accepted practice in the profession (4) consider other disorders as separated and distinct psychiatric diagnoses. The ICD-10 list of major categories is as follows:
Disorders Usually First Diagnosed in Infancy, Childhood, or Adolescence
Delirium, Dementia, and Amnestic and Other Cognitive Disorders
Mental Disorders Due to a General Medical Condition
Substance-Related Disorders
Schizophrenia and Other Psychotic Disorders
Mood Disorders
Anxiety Disorders
Somatoform Disorders
Factitious Disorders
Dissociative Disorders
Sexual and Gender Identity Disorders
Eating Disorders
Sleep Disorders
Impulse-Control Disorders Not Elsewhere Classified
Adjustment Disorders
Personality Disorders Many patients with dysthymic disorder have brain wave (EEG) abnormalities that mimic those found in major depression such as reduced REM latency, increased REM density, reduced slow-wave sleep, impaired sleep continuity. Patients with dysthymia who have these EEG abnormalities more frequently have a positive family history for major depression. They also respond better to antidepressant medications.

Anxiety disorders have scientific findings that differentiate them from depression and other psychiatric or psychological disorders. In patients with anxiety disorders functional neuroimaging shows abnormalities during symptom provocation tests, in the limbic, paralimbic and sensory association regions. Further, for anxiety there is a general theory of a neural behavioral-inhibition system. This system evaluates stimuli to attempt to determine their level of dangerousness and simultaneously in response produce behavioral inhibition and increase arousal and attention. Antianxiety drugs inhibit brain areas involved in these responses. From animal studies using pharmacological agents and/or brain lesions, anxiety is associated with several interconnected anatomical areas. Sensory stimuli that are interpreted as dangerous activate the hippocampus, especially the entorhinal cortex, which secondarily induces habituation by actions on the lateral and medial septal areas, which then stimulate the cingulate which induces behavioral inhibition. Several specific neurotransmitter systems influence this anxiety mechanism, including noradrenergic activity of the locus coeruleus, serotonergic systems originating in the raphe, and by widespread GABAA-receptor activity (which are the main locus of activity of the benzodiazepines). Stimuli that are interpreted as acute threats activate the "fight or flight" response, which is mediated especially by the locus coeruleus and the amygdala. The amygdala encodes fearful memories and aversive conditioning and participates in the acute fear and negative anticipation that we call anxiety. Further, intense anxiety stimulates the sympathetic nervous system via the locus coeruleus, and this induces tachycardia, tremor, and diaphoresis. The frontal cortex becomes aware of the anxiety and induces behavioral responses which are attempts to improve survival, but which often cause more harm and increase danger. The cingulate, in anxiety disorders, attempts to improve the communication between the cortex and the subcortical areas.

II. Methods of the Invention for Enhanced Treatment of Psychiatric Disorders

One embodiment of the present invention provides a method for enhanced treatment of a brain disorder characterized by neurologic or psychiatric disorder symptomology with a lateralized difference in hemispheric emotional valence, utilizing coordinated negative suppressive stimulation, comprising
 identifying a patient with a brain disorder;
 measuring a left hemispheric emotional valence for a left hemisphere of a brain of the patient and a right hemispheric emotional valence for a right hemisphere of the brain of the patient to identify a patient with a lateralized difference in hemispheric emotional valence;
 determining which hemisphere of the brain of the patient with a lateralized difference in hemispheric emotional valence has a more positive valence, and which hemisphere of the brain has a more negative valence;
 transcranially applying light energy having a wavelength of between about 300 nm to about 1500 nm and a power density at the scalp of up to about 10 W/cm$^2$ to the brain of said patient with the brain disorder with lateralized difference in hemispheric emotional valence, wherein the light energy is transcranially applied to the lateral forehead to activate (e.g., applied to) the underlying cortex of the brain hemisphere with a more positive valence for a defined period (e.g., greater than or equal to 15 seconds, e.g., greater than or equal to four minutes); and
 coordinated application of negative suppressive stimulation of the brain hemisphere with the more negative valence,
such that the brain disorder with lateralized difference in hemispheric emotional valence is treated in said patient. In certain embodiments, the frequency of treatment may range from several times a day to once a month. In particular embodiments, the transcranial application of light energy occurs for about 4 min. In particular embodiments, treatment is performed once per week.

In certain embodiments of the present invention the method further comprises sensory stimulation (e.g., vibratory) to the arm or leg contralateral to the brain hemisphere with the more positive valence, e.g., asymmetrically (i.e., without the identical stimulation in the ipsilateral arm or leg).

A. Identifying Patient With a Brain Disorder

The methods of the present invention comprise the step of identifying a patient with a brain disorder.

In certain embodiments, the brain disorder may be selected from the group consisting of depression, attention deficit disorder, schizophrenia, bipolar disorder, anxiety disorders, substance abuse disorders such as alcohol abuse and drug abuse, eating disorders such as anorexia and bulimia, phobias. Asperser's syndrome, dissociative disorders, insomnia, borderline personality disorder, general well-being, Alzheimer's Disease, Parkinson's Disease, Autism, Stroke and any combinations thereof.

In certain embodiments, the brain disorder includes one of persistent anxiety, anxiety attacks, feelings of panic, fears of social contacts, obsessive-compulsive disorder, phobias, post-traumatic stress disorder, and generalized anxiety disorder.

In one embodiment, the methods of the present invention may be used to treat the human brain for psychological, psychiatric, depressive, neurological, general well-being and other conditions. In one embodiment, the methods of the present invention may be used to treat depression. In one embodiment, the methods of the present invention may be used to treat psychiatric disorders other than depression including, but not limited to, attention deficit disorder, schizophrenia, bipolar disorder, anxiety disorders, substance abuse disorders such as alcohol abuse and drug abuse, eating disorders such as anorexia and bulimia, phobias, Asperser's syndrome, dissociative disorders, insomnia, borderline personality disorder or any combination thereof. In one embodiment, the methods of the present invention may be used to treat other psychiatric or psychological disorders including, but not limited to, persistent anxiety, anxiety attacks, feelings of panic, fears of social contacts, nightmares, flashbacks, alcohol or drug abuse, obsessive thoughts, compulsive behavior, attention disorder, sexual problem, eating disorder such as anorexia, bulimia or obesity, irrational thinking, or any combination thereof. In one embodiment, the methods of the present invention may be used to treat psychiatric disorders that are co-morbid or co-existent with depression. In one embodiment, the methods of the present invention may be used to treat more than one psychiatric disorder at a given time. For instance, the method may treat a patient having both depression and attention deficit disorder or a patient having both anorexia and insomnia. In one embodiment, the methods of the present invention may be used to benefit persons who do not have any psychological disorders. For patients without any of the above psychological disorders, the methods of the present invention may help improve their psychological well-being and enhance their positive outlook. These patients can find more appreciation for life, for themselves (improved self-esteem), their work, and their personal relationships. The methods of the present invention may improve patient self-confidence, positive disposition, interpersonal relationships, and/or quality of life. In certain embodiments, the methods may also assist in the diagnosis of brain disorders.

In certain embodiments of the present invention, the methods of the present invention may be used benefit patients with a history of opiate dependence by improving their psychological well-being, and/or reducing opioid cravings and use.

B. Measuring Hemispheric Emotional Valence

The methods of the present invention comprise the step of measuring a left hemispheric emotional valence for a left hemisphere of a brain of the patient and a right hemispheric emotional valence for a right hemisphere of the brain of the patient to identify a patient with a lateralized difference in hemispheric emotional valence. In this respect, the step of measuring hemispheric emotional valence (HEV), in certain embodiments may include the use of lateral visual field stimulation (LVFS).

In an embodiment, the methods of the present disclosure may include the use of glasses for the LVFS treatment, such as safety glasses or goggles, taped or covered so that they permit vision to only one lateral visual field at a time. The patient is asked to look to one side and to fixate the center of his vision on the edge of the tape so that he or she is looking out of the lateral half of one eye. Vision from the other eye is occluded by the tape on the other side. Any scale may be used to score this process that describes how a person feels on one side versus the other.

In certain embodiments, while looking out of the specific visual field, the patient is asked to look at a photograph of a man or woman with a mildly angry facial expression. After 45 seconds, he or she is asked to verbally rate his or her present feelings for each of 10 affects from Positive and Negative Affect Scale (PANAS), from none to extreme on a 5-point scale. Following the PANAS measurements, the patient is asked to rest for 1 minute looking straight ahead so that vision from both eyes is occluded. The patient is then asked to repeat the procedure by looking out of the second visual field. The PANAS has 5 positive affects including alert, inspired, determined, attentive, active and 5 negative affects including upset, hostile, ashamed, nervous, and afraid. For each visual field, the sum of the scores on the 5 negative affects is subtracted from the scores from the 5 positive effects and the difference is the PANAS score. The score measured when the person looks out of the right lateral visual field (RVF) is subtracted from the score measured when the person looks out of the left lateral visual field (LFV). The LVF is indicative of the state of the right hemisphere since the connection between the medial retinas and the cerebral hemispheres are crossed. Since a more positive PANAS score indicates more positive affect, we assign a value for the person's HEV according to the formula: LVF PANAS score—RVF PANAS. A positive score suggests that the right hemisphere has a more positive HEV. Research studies show that LVFS offers a good indication that the left and right cerebral hemispheres are generally associated with different emotional valences such that one hemisphere (either left or right) is associated with a more positive outlook on the world (positive hemispheric valence) and the other a more negative outlook on the world (negative hemispheric valence).

A person's personality and some of the person's psychological characteristics may be affected by which hemisphere, right or left hemisphere, dominates. The eyes are connected to the brain so that vision to the left side of a person goes first to the opposite (right) hemisphere and vision to the right side of a person goes first to the left hemisphere. One hemisphere can be stimulated over the other by restricting vision to a portion of the retina of an eye that is connected to a particular hemisphere of the brain. For instance, LVFS has been shown by fMRI to induce a very large increase in brain activity in the hemisphere opposite the visual field, when the subject looked out of the left visual field (LVF) and the right visual field (RVF). As an example, a person looking out of one visual field might see another person as very critical of him and he might feel very critical of himself. Looking out the opposite visual field he is apt to see another person as quite approving of him and he is apt to see himself positively.

C. Determining Hemispheric Positive Valence and Negative Valence

The methods of the present invention comprise the step of determining which hemisphere of the brain of the patient with a lateralized difference in hemispheric emotional valence has a more positive valence, and which hemisphere of the brain has a more negative valence.

In one embodiment, the PANAS score may be used to determine the hemisphere of the brain with a positive valence and the hemisphere of the brain with a negative valence.

D. Transcranial Application of Light Energy to Brain Hemisphere With More Positive Valence The methods of the present invention comprise the step of transcranially applying light energy having a wavelength of between about 300 nm to about 1500 nm and a power density at the scalp of up to about 10 W/cm$^2$ to the brain of said patient with the brain disorder with lateralized difference in hemispheric emotional valence, wherein the light energy is transcranially applied to the lateral forehead to activate the underlying cortex of the brain hemisphere with a more positive valence for a defined period.

This defined period would depend upon the specific wavelength and power density selected. The time period would also depend upon the frequency of treatment. In certain embodiments, the transcranial application of light energy may range from about 15 seconds to about 10 hours. In certain embodiments of the present invention, the methods of the present invention apply light energy to treat a hemisphere of the brain, e.g., near infrared light (NIR). In certain embodiments, light energy may have a wavelength of between about 300 nm to about 1500 nm. The present invention can use any source of light, whether low level laser or LED, so long as its duration and intensity are in accordance with the power density wavelength and form, as required herein. In particular embodiments, the NIR light may, in one embodiment, be applied using photobiomodulation (PBM) in the form of an LED.

In certain embodiments of the present invention, NIR light may be applied at a distance of about 0 to about 1000 mm from the skin. In certain embodiments, NIR light may be applied at a distance of about 0 mm from the skin. In certain other embodiments, NIR light may be applied at a distance of about 4 mm from the skin. For example, placing the NIR light at a distance of 0 mm or about 4 mm from the skin at a power density of about 250 mW/cm$^2$ allows an amount of NIR light and intensity to be directed at a person's brain without causing harm to the brain, e.g., during a 4-minute treatment at a given site. For example, this dose may be safely delivered to other sites on the head in the same treatment setting. It should be noted that the intensity of the NIR light increases as the NIR light approaches the skin and decreases in intensity by the square of the distance as the NIR light is moved away from the skin. As such, selecting the distance from the skin in certain embodiments shall account for the power density and the likelihood that the LED will emit heat that cannot be dissipated by the heat sink and fan. If the patient can detect heat, placebo-controlled studies may not be conducted as the patient may know whether the LED light was on or off; alternatively, placing a barrier like foil over the LED may allow heat but not photons to penetrate, to avoid this concern. Also, the heat from the LED might cause the patient to feel pain the closer the LED is to the patient. Additionally, too much light, without heat, can cause damage to the skin.

In certain embodiments of the present invention, the light energy that is transcranially applied to the lateral forehead to activate the underlying cortex of the brain hemisphere with a more positive valence has a wavelength of 810 nm (e.g., ±40 nm).

During treatment, the light treatment device may be pulsed, or the light treatment may be continuously applied. In an embodiment, the NIR light may be pulsed when applied to the skin of both hemispheres of the brain (e.g., at different rates to different effect). Pulsing the NIR light may be used to entrain the brain and thereby affect the state of the brain. A faster entrainment can increase brain activity, and a slower entrainment can decrease brain activity. In this way, in certain embodiments of the present invention the light applied to the more positive valence may be pulsed at fast rate (e.g., about 10 times a second), while light applied to the more negative valence may be pulsed at a slow rate (e.g., 2 to 4 times a second) for negative suppressive stimulation.

In certain embodiments of the present invention, the light energy that is transcranially applied to the lateral forehead to activate the underlying cortex of the brain hemisphere with the more positive valence comprises continuous wave light or light at a high pulse frequency; e.g., greater than about 10 Hz (e.g., about 10 times a second), e.g., greater than about 20 Hz, e.g., greater than about 40 Hz.

In certain embodiments of the present invention, the power density of the light at the scalp is up to 320 mW/cm² to the brain of said patient.

In certain embodiments of the present invention, the light output to the positive valence may be continuously applied, e.g., at about 250 mW/cm² at a wavelength of about 810 nm with a full width half maximum of about 40 nm. In certain embodiments, the NIR light may be directed at a person's brain for about 4 minutes (total delivered fluence per spot of about 60 J/cm²). In an embodiment, the procedure with the NIR light may be repeated at least at one other site on the forehead. In an embodiment, the NIR light may penetrate the dura, or the outermost of the three layers of the meninges surrounding the brain, at about 3.7%. In accordance with a penetration of about 3.7%, approximately 2.1 J/cm² of fluence is delivered to each of the treated areas of the brain.

E. Coordinated Application of Negative Suppressive Stimulation of Brain Hemisphere With More Negative Valence The methods of the present invention comprise the step of coordinated application of negative suppressive stimulation of the brain hemisphere with the more negative valence. In certain embodiments, the coordinated application of the negative suppressive stimulation is simultaneous with the transcranial application of light energy to the brain hemisphere with a more positive valence, i.e., during the defined period described above.

In certain embodiments of the present invention, the negative suppressive stimulation of the brain hemisphere with the more negative valence comprises transcranially applying pulsing light energy between about 300 nm to about 1500 nm and a power density at the scalp of up to about 10 W/cm² to the brain of said patient at a low frequency (e.g., about 2-4 Hz) ipsilateral to the brain hemisphere with the more negative valence, e.g., asymmetrically (i.e., without the identical stimulation in the contralateral brain hemisphere). In certain embodiments, the relatively slow pulsing LED is intended to decrease the EEG frequency and thereby decrease the activity of the targeted hemisphere by placing the LED over the hemisphere with the more negative HEV. Differences in pulsing frequency produce differences in total light energy being applied, where slower pulsing reduces total light energy delivered; and therefore, with two sources of light energy being used simultaneously on the different brain hemispheres, the differences in resulting light energy being delivered will be accounted for in the determination of the defined period of application and the selected wavelength and power density.

In certain embodiments of the present invention, the light energy that is transcranially applied to the lateral forehead to activate the underlying cortex of the brain hemisphere with the more negative valence has a wavelength of 810 nm (e.g., ±40 nm).

In certain embodiments of the present invention the negative suppressive stimulation of the brain hemisphere with the more negative valence comprises calmative auditory stimulation (e.g., music) of the ear contralateral to the brain hemisphere with the more negative valence, e.g., asymmetrically (i.e., without the identical stimulation in the ipsilateral ear). In certain embodiments, the auditory stimulation is playing calming music in the ear opposite the negative hemisphere to inhibit the negative hemisphere. In certain embodiments of the present invention, the negative suppressive stimulation of the brain hemisphere with the more negative valence comprises any combination of calmative auditory stimulation of the ear contralateral to the brain hemisphere with the more negative valence, and transcranially applying pulsing light energy at a low frequency (e.g., about 2-4 Hz) ipsilateral to the brain hemisphere with the more negative valence.

F. Combination Therapies

In certain embodiments, the methods of the present invention may be used in combination with any known or existing treatment. For example, the methods and devices of the present invention may be used in combination with other treatments for brain disorders like depression, including antidepressants and talk therapy. Other combination therapies may include, for example, electro-convulsive therapy, benzodiazepams (such as diazepam or klonazepam) which are common treatments for anxiety disorders, antipsychotic medications for schizophrenia, bisulfiram for the treatment of alcohol dependence, or buprenorphine for opiate dependence.

In certain embodiments, the methods of the present invention may be combined with other types of treatments for an improved therapeutic effect. For example, treatment can include directing light through the scalp of the patient to a target area of the brain concurrently with applying an electromagnetic field to the brain. The light may be applied with a desired power density and with a desired electromagnetic field strength at the target area.

III. Devices of the Invention for Enhanced Treatment of Psychiatric Disorders The methods of the present invention may be implemented using a variety of devices alone or in combination with other methods and/or devices. As such, one embodiment of the present invention provides a device for the enhanced treatment of a brain disorder characterized by neurologic or psychiatric disorder symptomology with a lateralized difference in hemispheric emotional valence.

Another embodiment of the present invention provides device for the enhanced treatment of a brain disorder characterized by neurologic or psychiatric disorder symptomology with a lateralized difference in hemispheric emotional valence, utilizing coordinated negative suppressive stimulation, comprising a light emitting diode (LED) for transcranial application of light energy having a wavelength of between about 300 nm to about 1500 nm and a power density at the scalp of up to about 10 W/cm$^2$ to the brain of a patient with a brain disorder characterized by neurologic or psychiatric disorder symptomology with a lateralized difference in hemispheric emotional valence, wherein the light emitting diode (LED) is suitable for asymmetric transcranial application to the forehead of the patient to activate (e.g., applied to) the underlying cortex of the brain hemisphere with a more positive valence for a selectable (defined) period of time and is suitable to coordinate with the application of negative suppressive stimulation of the brain hemisphere with the more negative valence effected through the incorporation and use of one or more of the following components:

a calmative auditory stimulation component (e.g., ear bud or localized speaker) designed to deliver asymmetric localized calmative sound (e.g., music) to the ear contralateral to the brain hemisphere with the more negative valence, or a pulsing light emitting diode (LED) for transcranial application of light energy capable of delivering light energy between about 300 nm to about 1500 nm and a power density at the scalp of up to about 10 W/cm$^2$ to the brain of said patient as low frequency pulsating light energy (e.g., about 2-4 Hz) ipsilateral to the brain hemisphere with the more negative valence, and wherein the negative suppressive stimulation is coordinated with the asymmetric transcranial application to the forehead of the patient to activate the underlying cortex of the brain hemisphere with the more positive valence. In certain embodiments, the device comprises both the calmative auditory stimulation component and the pulsing light emitting diode (LED).

In certain embodiments of the present invention, the device further comprises a power supply. In certain embodiments, the power supply is constructed so that the LED delivers 250 mW/cm$^2$ at the scalp. In certain embodiments the power supply may be in the form of a battery or it may be connected to a power outlet. In certain embodiments, the device shall be suitable for connection to the supply mains with a voltage between about 100 and about 240 VAC at frequencies of about 50 or about 60 Hz.

In certain embodiments of the present invention, the LED is attached to a heatsink and/or a fan for cooling.

In certain embodiments of the present invention, the LED is designed to operate at a temperature of less than or equal to about 48° C. In particular embodiments, the device comprises a sensor that shuts the LED off if the LED reaches a certain temperature, e.g., greater than about 48° C. In certain embodiments of the present invention, the device further comprises a thermometer that turns off the power at a defined temperature, e.g., exceeding a defined temperature.

In certain embodiments of the present invention, the LED comprises two or more sites positioned separately on the forehead. For example, in one embodiment, one LED may be used to treat one location on a patient's head at a given time.

In certain embodiments of the present invention, more than one LED can be used to treat more than one location on a patient's head at a given time In certain embodiments of the present invention, the LED comprises two sites positioned at each of 2 sites on the forehead that correspond to the 10-20 EEG sites, F3, and F4.

In certain embodiments of the present invention, the LED may be tuned to deliver a specified peak wavelength. In certain embodiments, the peak wavelength is 810 nm (e.g., ±40 nm).

In certain embodiments of the present invention, the LED is designed to be used in continuous mode or pulsed at various pulse frequencies.

In certain embodiments of the present invention, the device further comprises a sensory stimulation component designed to deliver vibration stimulation to the arm or leg contralateral to the brain hemisphere with the more positive valence.

In certain embodiments of the devices of present invention, the brain disorder may be selected from the group consisting of depression, attention deficit disorder, schizophrenia, bipolar disorder, anxiety disorders, substance abuse disorders such as alcohol abuse and drug abuse, eating disorders such as anorexia and bulimia, phobias, Asperser's syndrome, dissociative disorders, insomnia, borderline personality disorder, general well-being, Alzheimer's Disease, Parkinson's Disease, Autism, Stroke and any combinations thereof. In certain embodiments, the brain disorder includes one of persistent anxiety, anxiety attacks, feelings of panic, fears of social contacts, obsessive-compulsive disorder, phobias, post-traumatic stress disorder, and generalized anxiety disorder.

The methods of the present disclosure may affect blood flow within the brain. In this respect, blood flow in the brain may be measured in left and right frontal poles by NIRS, by a blood flow monitoring component, such as an adapted Somanetics INVOS system, modified by Somanetics to provide total hemoglobin (cHb); which may form a component of certain devices of the present invention. In an embodiment, the blood flow monitoring component uses a low power NIR LED. The blood flow monitoring component has no effect on the brain. In certain embodiments, the blood flow monitoring component measures the amount of blood in the brain once a second. In an embodiment, this component measures oxy- and deoxy-hemoglobin. The blood flow monitoring device component poses no harm or discomfort to subjects and allows subjects to have relatively free movement. The blood flow monitoring device component can be used to monitor cHb in the left and right frontal poles during tPBM.

EXEMPLIFICATION

Having thus described the invention in general terms, reference will now be made to exemplary embodiments, and the accompanying drawings of exemplary embodiments, which are not necessarily drawn to scale, and which are not intended to be limiting in any way.

In this respect, it is to be understood that the invention is not limited in its application to the details of construction and to the arrangements of the components set forth in the following description or illustrated in the Figures. The invention is capable of other embodiments and of being practiced and carried out in various ways. Also, it is to be understood that the phraseology and terminology employed herein are for the purpose of description and should not be regarded as limiting.

Example 1

Coordinated Negative Suppressive Stimulation

In two blinded, placebo-controlled studies, it was determined that unilateral transcranial photobiomodulation (IPBM) to the forehead over a hemisphere at F3 or F4 with a more positive hemispheric emotional valence (HEV) achieved highly significant reductions in opioid craving and in Hamilton Depression Rating Scales and Hamilton Anxiety Rating Scales. It was then further investigated to see if methods to not only activate the positive hemisphere, but also inhibit the negative hemisphere could significantly improve ratings of wellbeing minus distress (W-D) over what was achieved with stimulation of the positive hemisphere.

Prior to all treatments it was first determined which hemisphere had a more positive HEV and which, more negative and these methods will be described in the Methods section below.

A. Method

This study was a single site, sham-controlled study of 16 patients in the experimenter's private practice who were known to be positively responsive to unilateral tPBM which has become a part of their routine psychiatric care as an off-label augmentation to their on-going psychotherapy and medication. For each patient, the study took place in one session.

Inclusion criteria were that the patients were being treated with unilateral tPBM as an off-label adjunctive treatment integrated with their ongoing psychotherapy and medication management. Sixteen sequential patients who had been having a very positive response to the unilateral tPBM were enrolled. They were all on medication, including buprenorphine, and all had multiple diagnoses, and all had a history of opioid abuse, complex PTSD, anxiety and depression and all had had a positive response to their ongoing treatment, and none were disabled. All were abstinent for at least 6 months of illicit substances by urine drug screens and all were having only mild to moderate symptoms. Their demographic information is presented in Table 1.

Patients were recruited without regard to gender or ethnicity and were enrolled on a first come basis. Exclusion criteria were a history of a neurological condition (e.g., epilepsy, traumatic brain injury, or stroke), pregnancy, any current acute or chronic medical condition that might confound the study or an impaired decision-making capacity. In this study, no patient who was asked to participate declined and no patient was excluded.

TABLE 1

Demographic characteristics of study patients. All had suffered in the past opioid use disorder (OUD), major depression (MD), anxiety disorder (AD), and post-traumatic stress disorder (PTSD).

| Patient # | Age | Gender | Handedness | OUD | MD | AD | PTSD |
|---|---|---|---|---|---|---|---|
| 1 | 40 | m | R | y | y | y | y |
| 2 | 36 | m | R | y | y | y | y |
| 3 | 35 | m | R | y | y | y | y |
| 4 | 37 | m | L | y | y | y | y |
| 5 | 30 | m | R | y | y | y | y |
| 6 | 31 | m | R | y | y | y | y |
| 7 | 42 | m | R | y | y | y | y |
| 8 | 39 | m | R | y | y | y | y |
| 9 | 37 | m | R | y | y | y | y |
| 10 | 40 | m | R | y | y | y | y |
| 11 | 46 | f | L | y | y | y | y |
| 12 | 56 | m | R | y | y | y | y |
| 13 | 31 | f | R | y | y | y | y |
| 14 | 45 | m | R | y | y | y | y |
| 15 | 62 | m | R | y | y | y | y |
| 16 | 63 | f | R | y | y | y | y |

The sixteen patients known to be responsive to unilateral tPBM were treated with 4 different modalities presented in random order following a 2½ minute unilateral tPBM, near infrared mode treatment to a hemisphere with a more positive hemispheric emotional valence (HEV). All responded positively to the unilateral tPBM and it was determined if 2 modalities thought to inhibit the hemisphere with the more negative HEV would improve scores of "wellbeing minus distress" (W-D) beyond the improvement achieved by unilateral tPBM to the side of the forehead over the hemisphere with the more positive HEV.

These coordinated negative suppressive stimulation modalities were
1) to use negative suppressive stimulation of calmative auditory stimulation of the ear contralateral to the brain hemisphere with the more negative valence by playing pleasant and calming classical music in the ear contralateral to the more negative hemisphere to attempt to calm or inhibit that hemisphere. In this study Elgar's Variations on an Original Theme, Op. 36 "Enigma," was used. As a comparison modality, another modality was employed by playing the identical music in the ear ipsilateral to the more negative hemisphere, which likely has an inhibitory effect on the more positive hemisphere; and
2) to attempt to inhibit the more negative hemisphere by placing a unilateral tPBM over the that hemisphere with the same parameters as that used to stimulate the more positive hemisphere, except that the LED was pulsed at 2 Hz ((2 pulses a second), which through entrainment is believed to inhibit the negative hemisphere (e.g., with the intent of reducing brain activity by entraining it to a slow rhythm by pulsating the light at 2 Hz). As a comparison, a sham tPBM LED was applied over the negative hemisphere. The sham was the identical pulsating LED, but with aluminum foil over the LED.

Improvements in wellbeing were measured by a Wellness Scale, which asks patients to measure their subjective sense of wellbeing from 0 to 9 and their sense of distress from 0 to 9 immediately at the time of testing and subtracting the distress score, from 0 to 9, from the wellbeing score to arrive at a W-D score. All of the subjects in the study had consistently reported improvements in the Wellness Scale from unilateral tPBM over the forehead over the cerebral hemisphere that had been determined to be more positive by our two test for HEV described below. In this respect, the purpose of this study was to determine if methods to simultaneously inhibit the negative hemisphere would further improve the Wellbeing Scale scores. Here it is being explored whether activating the positive hemisphere and inhibiting the negative (which can be left or right sided, determined by the HEV tests), improves outcomes as measured by the Wellness Scale.

The 2 tests for HEV are the lateral visual field test (LVFT) and a novel computer test for HEV (CTHEV), which are the subject of U.S. patent application Ser. No. 16/703,937. The LVFT consisted of asking each patient to put on taped safety goggles that allowed vision out of only the left visual field, when the patient looked as far as possible to the left, or the right visual field when the patient looked to the right. While looking out of each visual field the patient was asked to rate from 0 to 10 his level of anxiety or distress while he looked at a photograph of a very angry man, designed so that each half of the face was identical. The CTHEV, showed a video of alternating, symmetrical photographs of angry men to one visual field (by having the patient fixate on a central dot for 1 minute) after which the patient was asked to rate from 0 to 10 his level of anxiety or distress. As with the LVFT, the CTHEV was then repeated to the other visual field and the side with the lower scores was considered the positive visual field, which suggested that the contralateral hemisphere was the positive hemisphere. The HEV with either test was the numeric difference between the recorded scores from each visual field.

The Wellness Scale consisted of 2 questions asked of the patient to assess his immediate feelings of wellbeing and distress. The first questions was: How much wellbeing from 0 to 9 do you feel at this moment? And the second questions was: How much distress or anxiety do you feel at this moment from 0 to 9. The final score is the W–D score which is the wellness sore minus the distress score.

Each patient was treated for 2.5 minutes with unilateral tPBM over the forehead on the side of the hemisphere with the more positive HEV. At 2.5 minutes into the treatment after the patient reported their W–D score, while the unilateral tPBM to the positive hemisphere continued, the patient was then given each of 4 additional treatments for 2 minutes in random order (randomized by random numbers). After each additional 2-minute treatment the patient was asked to score his Wellness Scale. Of the 4 treatments, 2 were intended to reduce the activity of the negative hemisphere through negative suppressive stimulation and each of these had a comparison treatment that was not expected to reduce the activity of the negative hemisphere.

The active treatment consisted of applying continuous, non-pulsating tPBM from a light emitting diode (LED) (Marubeni America Corp, Santa Clara, CA) with a peak wavelength of 810 nm (±40 nm), delivering 250 mW/cm$^2$ when applied at the skin. tPBM for 4 minutes (total delivered fluence per site of 60 J/cm$^2$) at each of 2 sites on the forehead that correspond to the 10-20 EEG sites, F3, and F4. Based on a penetration of 3.7% of the light to the dura, it was calculated that 2.1 J/cm$^2$ was delivered to each of the treated areas of the brain. The level of light exposure at the skin was well below the irradiance allowed by the ANSI standard of 320 mW/cm$^2$. The New England IRB in 2019 and the Partners IRB in 2009 both determined that the device posed no significant risk. In other published tPBM studies no significant side effects have been reported to date.

The LED was attached to a heatsink and a fan for cooling. When operating the temperature was always below 104° F. The power supply was constructed by a product engineer so that the LED would deliver 250 mW/cm$^2$ at the skin. The engineer arranged for the LED to be used in continuous mode or pulsed at various pulse frequencies. To inhibit the negative hemisphere the device was pulsed at 2 Hz. The sham device was the same pulsed device covered with aluminum foil so that the patient felt the same warmth but received no light as verified by a photon detector. In this and other trials, subjects could not detect whether they were receiving active or sham treatment other than by their psychological response.

B. Results

Table 2. Shows their individual results to the Wellness Scale for the baseline tPBM treatment to the positive hemisphere and to the 4 supplemental treatments to the negative hemisphere.

TABLE 2

The raw data for the Wellness-Distress scores for each of the 16 patients.

| Patient # | W-D 1 tPBM | W-D 2 contra ear | W-D 3 ipsi ear | W-D 4 active pulse | W-D 5 sham pulse |
|---|---|---|---|---|---|
| 1 | 4 | 5 | 2 | 4 | 4 |
| 2 | 3 | 5 | 1 | 0 | 3 |
| 3 | 7 | 9 | 4 | 8 | 7 |
| 4 | 5 | 6 | 3 | 4 | 5 |
| 5 | 3 | 5 | 2 | 6 | 3 |
| 6 | 4 | 5 | 2 | 4 | 3 |
| 7 | 2 | 6 | 0 | 2 | 2 |
| 8 | 4 | 5 | 3 | 6 | 6 |
| 9 | 3 | 5 | 1 | 4 | 3 |
| 10 | 6 | 7 | 4 | 8 | 6 |
| 11 | 4 | 5 | 3 | 7 | 3 |
| 12 | 5 | 6 | 3 | 6 | 3 |
| 13 | 3 | 5 | 2 | 3 | 3 |
| 14 | 4 | 5 | 3 | 4 | 4 |
| 15 | 3 | 6 | 1 | 5 | 4 |
| 16 | 5 | 6 | 2 | 7 | 6 |
| mean | 4.1 | 5.7 | 2.3 | 4.9 | 4.1 |
| stand deviation | 1.3 | 1.1 | 1.1 | 2.2 | 1.5 |

Figure 1:
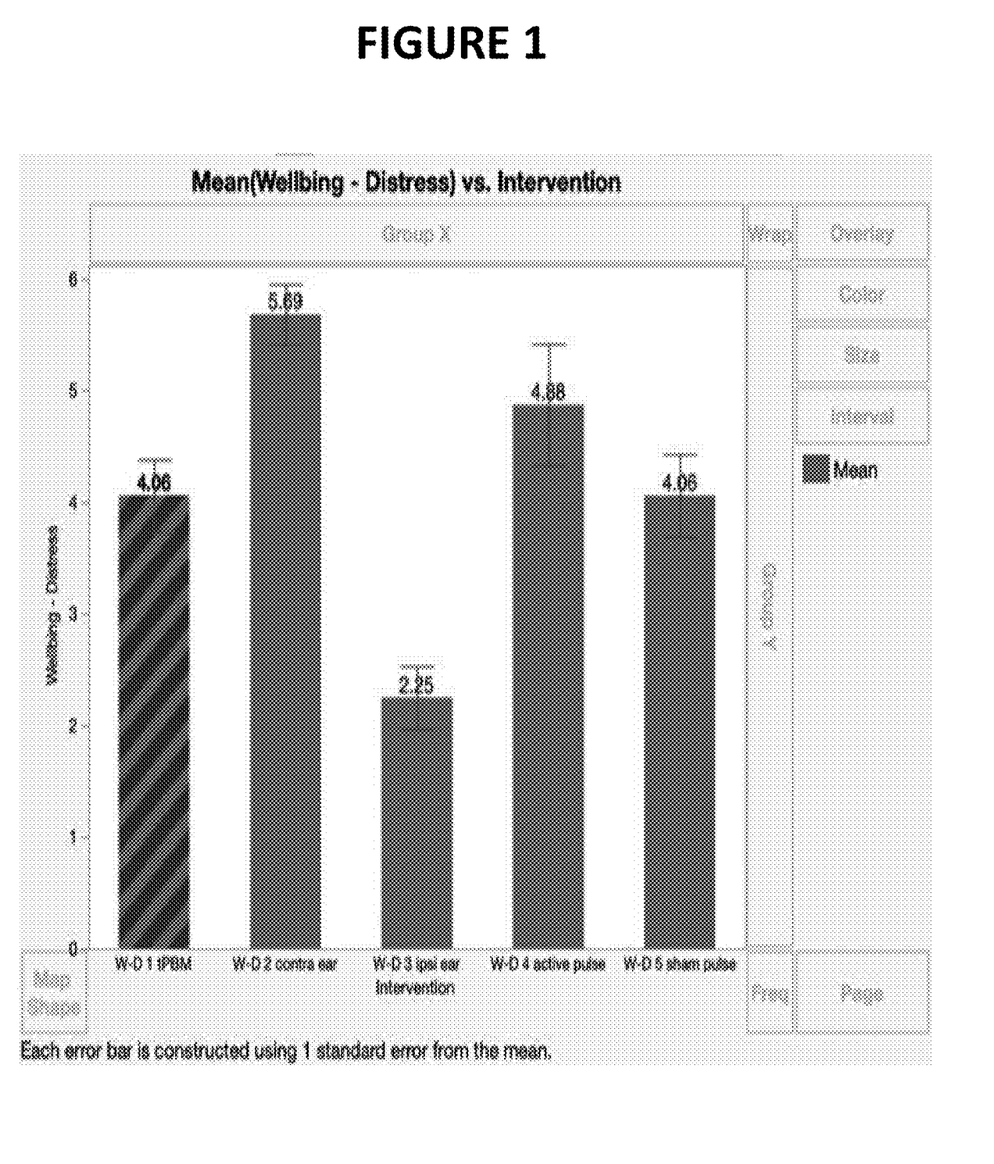
FIG. 1 shows a graph of the Wellness Scale for tPBM to the positive hemisphere, showing the mean and standard error data for the baseline and each of the 4 test condition coordinated treatments. Further statistical differences are shown in Table 3.
Figure 2:
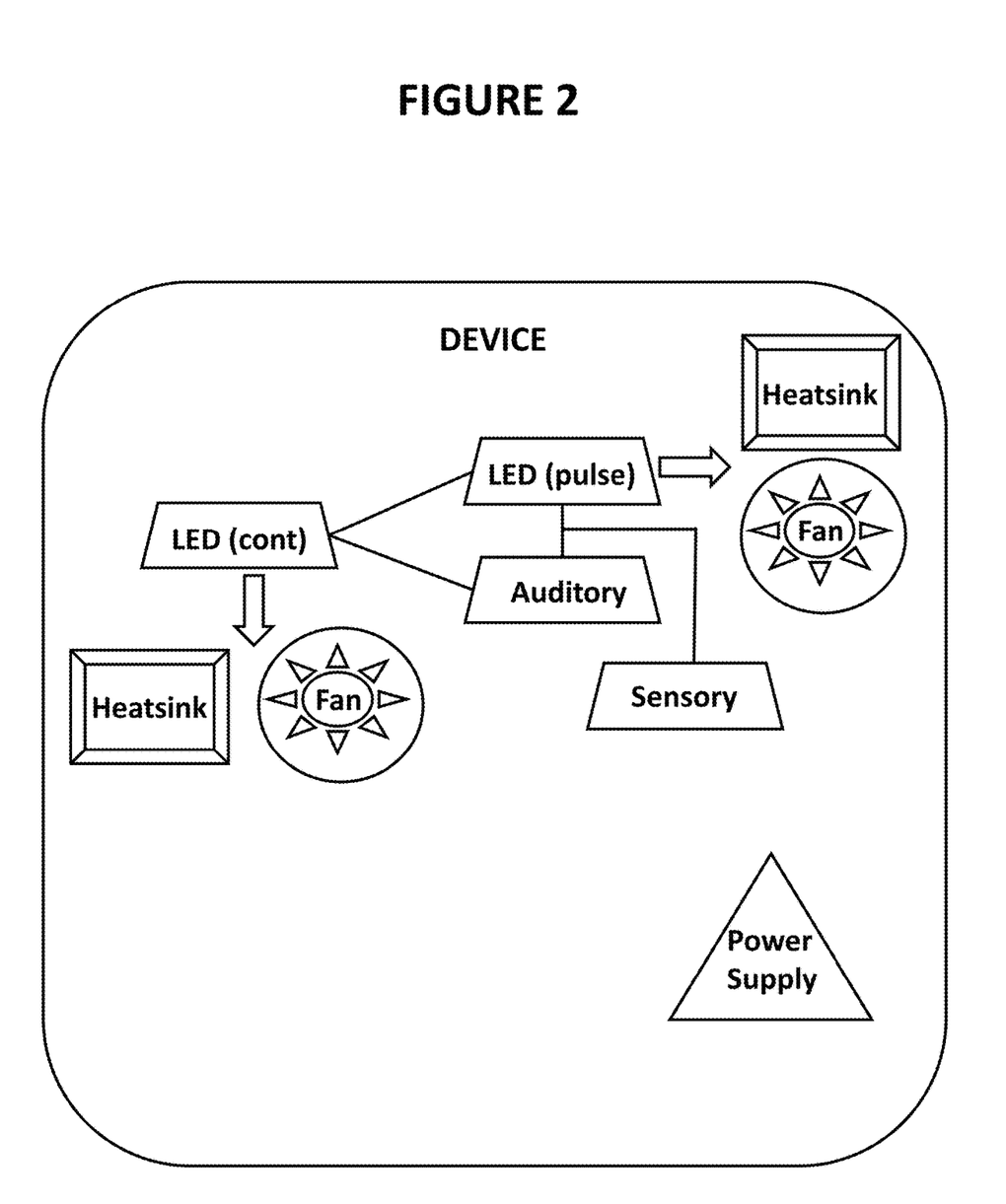
FIG. 2 represents an exemplary embodiment of a device of the present invention comprising a continuous non-pulsating LED applied in combination with a pulsating LED or auditory stimulation component. The exemplary embodiment of the device comprises a power supply and is shown with each LED (continuous and pulsating) associated with a heatsink and fan, and further comprising a sensory stimulation component.

FIG. 1 shows a graph of the mean and standard error data for the baseline and each of the 4 supplemental treatments. Table 2 shows the results of the paired-t tests.

TABLE 3

Matched Pairs t-tests

1. Difference: W-D contra ear – W-D tPBM

| W-D contra ear | 5.6875 | t-Ratio | 7.344125 |
|---|---|---|---|
| W-D tPBM | 4.0625 | DF | 15 |
| Mean Difference | 1.625 | Prob > \|t\| | <.0001 |
| Std Error | 0.22127 | Prob > t | <.0001 |
| Upper 95% | 2.09662 | Prob < t | 1.0000 |
| Lower 95% | 1.15338 | | |
| N 16 | | | |
| Correlation | 0.73431 | | |

2. Difference: W-D ipsilateral ear – W-D tPBM

| W-D ipsi ear | 2.25 | t-Ratio | −11.0669 |
|---|---|---|---|
| W-D tPBM | 4.0625 | DF | 15 |
| Mean Difference | −1.8125 | Prob > \|t\| | <.0001 |
| Std Error | 0.16378 | Prob > t | 1.0000 |
| Upper 95% | −1.4634 | Prob < t | <.0001 |
| Lower 95% | −2.1616 | | |
| N 16 | | | |
| Correlation | 0.86139 | | |

TABLE 3-continued

Matched Pairs t-tests

3. Difference: W-D ipsilateral ear – W-D 2 contra ear

| | | | |
|---|---|---|---|
| W-D ipsi ear | 2.25 | t-Ratio | −11.9265 |
| W-D contra ear | 5.6875 | DF | 15 |
| Mean Difference | −3.4375 | Prob > \|t\| | <.0001 |
| Std Error | 0.28822 | Prob > t | 1.0000 |
| Upper 95% | −2.8232 | Prob < t | <.0001 |
| Lower 95% | −4.0518 | | |
| N 16 | | | |
| Correlation | 0.45325 | | |

4. Difference: W-D 4 active pulse – W-D tPBM

| | | | |
|---|---|---|---|
| W-D 4 active pulse | 4.875 | t-Ratio | 2.085234 |
| W-D tPBM | 4.0625 | DF | 15 |
| Mean Difference | 0.8125 | Prob > \|t\| | 0.0545 |
| Std Error | 0.38964 | Prob > t | 0.0273 |
| Upper 95% | 1.64301 | Prob < t | 0.9727 |
| Lower 95% | −0.018 | | |
| N 16 | | | |
| Correlation | 0.71218 | | |

5. Difference: W-D sham pulse – W-D tPBM

| | | | |
|---|---|---|---|
| W-D 5 sham pulse | 4.0625 | t-Ratio | 0 |
| W-D tPBM | 4.0625 | DF | 15 |
| Mean Difference | 0 | Prob > \|t\| | 1.0000 |
| Std Error | 0.22361 | Prob > t | 0.5000 |
| Upper 95% | 0.47661 | Prob < t | 0.5000 |
| Lower 95% | −0.4766 | | |
| N 16 | | | |
| Correlation | 0.80034 | | |

6. Difference: W-D 5 sham pulse – W-D 4 active pulse

| | | | |
|---|---|---|---|
| W-D 5 sham pulse | 4.0625 | t-Ratio | −1.93221 |
| W-D 4 active pulse | 4.875 | DF | 15 |
| Mean Difference | −0.8125 | Prob > \|t\| | 0.0724 |
| Std Error | 0.4205 | Prob > t | 0.9638 |
| Upper 95% | 0.08378 | Prob < t | 0.0362 |
| Lower 95% | −1.7088 | | |
| N 16 | | | |
| Correlation | 0.64026 | | |

By analyzing paired t-tests it was shown that there were highly significant improvements with the contralateral music (p<0.001), from W–D of 4.1 (SD 1.3) to 6.1 (SD 1.3), but not the ipsilateral which actually caused a significant decrease in W–D (p<0.001) from 4.1 to 2.2 (SD=1.1). The slow pulsating LED over the negative side also improved W–D from 4.1 to 5.2 (SD=2.5), p=0.02, and the sham pulsing LED did not improve or diminish the W–D.

All of the statistical tests were selected and conducted using JMP. The main statistical tests were a paired t-test, a repeated measures analysis, and an independent samples t-test, depending on the statistical need. Since the objective of most tests was to compare outcomes in the same individuals under 2 conditions, active and sham, a paired t-test or repeated measures analysis was most often used. Because the hypothesis was that the active condition would obtain better clinical results, one-sided tests were used.

No patient reported any negative effects form any of the treatments at the time of testing or at ongoing follow-up C. Conclusion It was therefore conclusively shown that treating the hemisphere with the more negative HEV with coordinated negative suppressive stimulation modality, added to the clinical benefit of unilateral tPBM to the positive hemisphere. As such, a device which both stimulates the positive hemisphere and inhibited the negative would improve clinical outcomes for wellbeing and offer enhanced treatment for psychiatric disorders.

References

F. Schiffer, M. Teicher, C. Anderson, A. Tomoda, A. Polcari, C. Navalta, and S. Andersen, Determination of hemispheric emotional valence in individual subjects: a new approach with reasearch and therapeutic implications. Behav Brain Funct 3 (2007) 13.

F. Schiffer, Of Two Minds: The Revolutionary Science of Dual-Brain Psychology, The Free Press, New York, 1998.

F. Schiffer, Can the Different Cerebral Hemispheres Have Distinct Personalities? Evidence and Its Implications for Theory and Treatment of PTSD and Other Disorders. J Trauma Dissociation 1 (2000) 83-104.

F. Schiffer, Unilateral Transcranial Near Infrared Treatments for Opiate Addiction in a Clinical Practice . . . In Submission (2020).

F. Schiffer, Method for Using Therapeutic Glasses for Stimulating a Change in the Psychological State of a Subject., Schiffer, F, 1999.

F. Schiffer, Therapeutic Glasses and Method for Using The Same, 2000.

F. Schiffer, Method and Apparatus for Determining Hemispheric Emotional Valence, 2019.

F. Schiffer, Kahn, A., Ohashi, K., Hernandez, L., Anderson, C. M., Teicher, M. H., A Computerized Test for Hemispheric Emotional Valence Correlates with Lateralized Nucleus Accumbens and Amygdala Volumes by Anatomical MRI. In Submission (2020).

F. Schiffer, Methods for treating psychiatric disorders using light energy., Schiffer, F, 2012.

F. Schiffer, Methods for treating psychiatric disorders using light energy, Schiffer, F, 2013.

R. B. Pelka, C. Jaenicke, and J. Gruenwald, Impulse magnetic-field therapy for insomnia: a double-blind, placebo-controlled study. Adv Ther 18 (2001) 174-80.

M. Reite, L. Higgs, J. P. Lebet, A. Barbault, C. Rossel, N. Kuster, U. Dafni, D. Amato, and B. Pasche, Sleep inducing effect of low energy emission therapy. Bioelectromagnetics 15 (1994) 67-75.

'N.I.o.D. Abuse, Fiscal Year 2018 Budget Information-Congressional Justification for National Institute on Drug Abuse, 2018.

G. B. D. Disease, I. Injury, and C. Prevalence, Global, regional, and national incidence, prevalence, and years lived with disability for 354 diseases and injuries for 195 countries and territories, 1990-2017: a systematic analysis for the Global Burden of Disease Study 2017. Lancet 392 (2018) 1789-1858.

R. A. Rudd, L. J. Paulozzi, M. J. Bauer, R. W. Burleson, R. E. Carlson, D. Dao, J. W. Davis, J. Dudek, B. A. Eichler, J. C. Fernandes, A. Fondario, B. Gabella, B. Hume, T. Huntamer, M. Kariisa, T. W. Largo, J. Miles, A. Newmyer, D. Nitcheva, B. E. Perez, S. K. Proescholdbell, J. C. Sabel, J. Skiba, S. Slavova, K. Stone, J. M. Tharp, T. Wendling, D.

Wright, A. M. Zehner, C. Centers for Disease, and Prevention, Increases in heroin overdose deaths—28 States, 2010 to 2012. MMWR Morb Mortal Wkly Rep 63 (2014) 849-54.

R. A. Rudd, P. Seth, F. David, and L. Scholl, Increases in Drug and Opioid-Involved Overdose Deaths—United States, 2010-2015. MMWR Morb Mortal Wkly Rep 65 (2016) 1445-1452.

P. Seth, L. Scholl, R. A. Rudd, and S. Bacon, Overdose deaths involving opioids, cocaine, and psychostimulants—United States, 2015-2016. American journal of transplantation: official journal of the American Society of Transplantation and the American Society of Transplant Surgeons 18 (2018) 1556-1568.
F. Schiffer, Unilateral Transcranial Near Infrared Treatments for Opiate Addiction in a Clinical Practice. In Submission (2020).
F. Schiffer, A. L. Johnston, C. Ravichandran, A. Polcari, M. H. Teicher, R. H. Webb, and M. R. Hamblin, Psychological benefits 2 and 4 weeks after a single treatment with near infrared light to the forehead: a pilot study of 10 patients with major depression and anxiety. Behav Brain Funct 5 (2009) 46.
J. Wang, X. Wu, W. Lai, E. Long, X. Zhang, W. Li, Y. Zhu, C. Chen, X. Zhong, Z. Liu, D. Wang, and H. Lin, Prevalence of depression and depressive symptoms among outpatients: a systematic review and meta-analysis. BMJ Open 7 (2017) e017173.
B. Zia, M. J. Heisel, S. B. Peckham, and S. Rosen, A Psychometric Assessment of the Suicidal Behaviors Questionnaire (SBQ-5) and Geriatric Suicide Ideation Scale-Screen (GSIS-screen) in Middle-Aged and Older Men. Clin Gerontol 43 (2020) 46-60.
M. Marthoenis, A. Ilyas, H. Sofyan, and M. Schouler-Ocak, Prevalence, comorbidity and predictors of post-traumatic stress disorder, depression, and anxiety in adolescents following an earthquake. Asian J Psychiatr 43 (2019) 154-159.
F. Salehpour, J. Mahmoudi, F. Kamari, S. Sadigh-Eteghad, S. H. Rasta, and M. R. Hamblin, Brain Photobiomodulation Therapy: a Narrative Review. Molecular neurobiology 55 (2018) 6601-6636.
J. C. Rojas, and F. Gonzalez-Lima, Neurological and psychological applications of transcranial lasers and LEDs. Biochemical pharmacology 86 (2013) 447-57.
P. Cassano, S. R. Petrie, M. R. Hamblin, T. A. Henderson, and D. V. Iosifescu, Review of transcranial photobiomodulation for major depressive disorder: targeting brain metabolism, inflammation, oxidative stress, and neurogenesis. Neurophotonics 3 (2016) 031404.
M. A. Caldieraro, and P. Cassano, Transcranial and systemic photobiomodulation for major depressive disorder: A systematic review of efficacy, tolerability and biological mechanisms. J Affect Disord 243 (2019) 262-273.
D. W. Barrett, and F. Gonzalez-Lima, Transcranial infrared laser stimulation produces beneficial cognitive and emotional effects in humans. Neuroscience 230 (2013) 13-23.
M. R. Hamblin, Shining light on the head: Photobiomodulation for brain disorders. BBA Clin 6 (2016) 113-124.
F. Schiffer, Affect changes observed with right versus left lateral visual field stimulation in psychotherapy patients: possible physiological, psychological, and therapeutic implications. Compr Psychiatry 38 (1997) 289-295.
F. Schiffer, Of Two Minds: The Revolutionary Science of Dual-Brain Psychology, The Free Press, New York, 1998.
F. Schiffer, C. Anderson, and M. Teicher, EEG, Bilateral Ear Temperature, and Affect Changes Induced by Lateral Visual Field Stimulation. Compr Psychiatry 40 (1999) 221-225.
F. Schiffer, Can the Different Cerebral Hemispheres Have Distinct Personalities? Evidence and Its Implications for Theory and Treatment of PTSD and Other Disorders. J Trauma Dissociation 1 (2000) 83-104.
F. Schiffer, E. Zaidel, J. Bogen, and S. Chasan-Taber, Different psychological status in the two hemispheres of two split brain patients. Neuropsychiatry Neuropsychol Behav Neurol 11 (1998) 151-156.
F. Schiffer, F. Mottaghy, R. P. Vimal, P. R. P F, R. Cowan, A. Pascual-Leone, M. Teicher, E. Valente, and M. Rohan, Lateral visual field stimulation reveals extrastriate cortical activation in the contralateral hemisphere: an fMRI study. Psychiatry Res 131 (2004) 1-9.
F. Schiffer, M. Teicher, C. Anderson, A. Tomoda, A. Polcari, C. Navalta, and S. Andersen, Determination of hemispheric emotional valence in individual subjects: a new approach with reasearch and therapeutic implications. Behav Brain Funct 3 (2007) 13.
F. Schiffer, I. Glass, J. Lord, and M. H. Teicher, Prediction of clinical outcomes from rTMS in depressed patients with lateral visual field stimulation: a replication. J Neuropsychiatry Clin Neurosci 20 (2008) 194-200.
F. Schiffer, Z. Stinchfield, and A. Pascual-Leone, Prediction of Clinical Response to Transcranial Magnetic Stimulation for Depression by Baseline Lateral Visual Stimulation. Neuropsychiatry, Neuropsychology, and Behavioral Neurology 15 (2002) 18-27.
P. Cassano, S. R. Petrie, D. Mischoulon, C. Cusin, H. Katnani, A. Yeung, L. De Taboada, A. Archibald, E. Bui, L. Baer, T. Chang, J. Chen, P. Pedrelli, L. Fisher, A. Farabaugh, M. R. Hamblin, J. E. Alpert, M. Fava, and D. V. Iosifescu, Transcranial Photobiomodulation for the Treatment of Major Depressive Disorder. The ELATED-2 Pilot Trial. Photomed Laser Surg (2018).
Y. Lampl, J. Zivin, M. Fisher, R. Lew, L. Welin, B. Dahlof, P. Borenstein, B. Andersson, J. Perez, C. Caparo, S. llic, and U. Oron, Infrared Laser Therapy for Ischemic Stroke: A New Treatment Strategy. Results of the NeuroThera Effectiveness and Safety Trial-1 (NEST-1). Stroke (2007).
F. Schiffer, F. Mottaghy, R. Vimal, P. Renshaw, R. Cowan, A. Pascual-Leone, M. Teicher, L. Valente, and M. Rohan, Lateral Visual Field Stimulation Reveals Extrastriate Cortical Activation In The Contralateral Hemisphere: An fMRI Study. Psychiatry Res: Neuroimaging 131 (2004) 1-9'.
P. Cassano, C. Dording, G. Thomas, S. Foster, A. Yeung, M. Uchida, M. R. Hamblin, E. Bui, M. Fava, D. Mischoulon, and D. V. Iosifescu, Effects of transcranial photobiomodulation with near-infrared light on sexual dysfunction. Lasers Surg Med 51 (2019) 127-135.
L. L. Chao, Improvements in Gulf War Illness Symptoms After Near-Infrared Transcranial and Intranasal Photobiomodulation: Two Case Reports. Mil Med (2019).
E. Eshaghi, S. Sadigh-Eteghad, G. Mohaddes, and S. H. Rasta, Transcranial photobiomodulation prevents anxiety and depression via changing serotonin and nitric oxide levels in brain of depression model mice: A study of three different doses of 810 nm laser. Lasers Surg Med (2019).
C. Hamilton, D. Hamilton, F. Nicklason, N. El Massri, and J. Mitrofanis, Exploring the use of transcranial photobiomodulation in Parkinson's disease patients. Neural Regen Res 13 (2018) 1738-1740.
F. Salehpour, and S. H. Rasta, The potential of transcranial photobiomodulation therapy for treatment of major depressive disorder. Rev Neurosci 28 (2017) 441-453.
R. Zomorrodi, G. Loheswaran, A. Pushparaj, and L. Lim, Pulsed Near Infrared Transcranial and Intranasal Photobiomodulation Significantly Modulates Neural Oscillations: a pilot exploratory study. Sci Rep 9 (2019) 6309.
JMP®, Version 15, SAS Institute Inc, Cary, NC, 1989-2019.

Incorporation by Reference

The entire contents of all patents, published patent applications and other references cited herein are hereby expressly incorporated herein in their entireties by reference.

Equivalents

Those skilled in the art will recognize, or be able to ascertain using no more than routine experimentation, numerous equivalents to the specific procedures described herein. Such equivalents were considered to be within the scope of this invention and are covered by the following claims. Moreover, any numerical or alphabetical ranges provided herein are intended to include both the upper and lower value of those ranges. In addition, any listing or grouping is intended, at least in one embodiment, to represent a shorthand or convenient manner of listing independent embodiments; as such, each member of the list should be considered a separate embodiment.

What is claimed is:

1. A method for enhanced treatment of a brain disorder characterized by neurologic or psychiatric disorder symptomology with a lateralized difference in hemispheric emotional valence, utilizing coordinated negative suppressive stimulation, comprising
    identifying a patient with a brain disorder;
    measuring a left hemispheric emotional valence for a left hemisphere of a brain of the patient and a right hemispheric emotional valence for a right hemisphere of the brain of the patient to identify a patient with a lateralized difference in hemispheric emotional valence;
    determining which hemisphere of the brain of the patient with a lateralized difference in hemispheric emotional valence has a more positive valence, and which hemisphere of the brain has a more negative valence;
    transcranially applying light energy having a wavelength of between 300 nm to 1500 nm and a power density at the scalp of up to 10 $W/cm^2$ to the brain of said patient with the brain disorder with lateralized difference in hemispheric emotional valence, wherein the light energy is asymmetrically transcranially applied to the lateral forehead to activate the underlying cortex of the brain hemisphere with a more positive valence for a defined period; and
    coordinated application of negative suppressive stimulation of the brain hemisphere with the more negative valence, wherein the negative suppressive stimulation is coordinated with the asymmetric transcranial application to the forehead of the patient to activate the underlying cortex of the brain hemisphere with the more positive valence,
such that the brain disorder with lateralized difference in hemispheric emotional valence is treated in said patient.

2. The method for enhanced treatment of claim 1, wherein the negative suppressive stimulation of the brain hemisphere with the more negative valence comprises calmative auditory stimulation of the ear contralateral to the brain hemisphere with the more negative valence.

3. The method for enhanced treatment of claim 1, wherein the negative suppressive stimulation of the brain hemisphere with the more negative valence comprises transcranially applying pulsing light energy between 300 nm to 1500 nm and a power density at the scalp of up to 10 $W/cm^2$ to the brain of said patient at a low frequency ipsilateral to the brain hemisphere with the more negative valence.

4. The method for enhanced treatment of claim 1, wherein the negative suppressive stimulation of the brain hemisphere with the more negative valence comprises any combination of calmative auditory stimulation of the ear contralateral to the brain hemisphere with the more negative valence, and transcranially applying pulsing light energy at a low frequency ipsilateral to the brain hemisphere with the more negative valence.

5. The method for enhanced treatment of claim 1, wherein the light energy that is transcranially applied to the lateral forehead to activate the underlying cortex of the brain hemisphere with the more positive valence comprises continuous wave light or light at a high pulse frequency.

6. The method for enhanced treatment of claim 1, further comprising sensory stimulation to the arm or leg contralateral to the brain hemisphere with the more positive valence.

7. The method for enhanced treatment of claim 1, wherein the power density of the light at the scalp is up to 320 $mW/cm^2$ to the brain of said patient.

8. The method for enhanced treatment of claim 1, wherein the light energy that is transcranially applied to the lateral forehead to activate the underlying cortex of the brain hemisphere with a more positive valence has a wavelength of 810 nm.

9. The method for enhanced treatment of claim 1, wherein the brain disorder may be selected from the group consisting of depression, attention deficit disorder, schizophrenia, bipolar disorder, anxiety disorders, substance abuse disorders such as alcohol abuse and drug abuse, eating disorders such as anorexia and bulimia, phobias, Asperser's syndrome, dissociative disorders, insomnia, borderline personality disorder, general well-being, Alzheimer's Disease, Parkinson's Disease, Autism, Stroke and any combinations thereof.

10. The method for enhanced treatment of claim 9, wherein the brain disorder includes one of persistent anxiety, anxiety attacks, feelings of panic, fears of social contacts, obsessive-compulsive disorder, phobias, post-traumatic stress disorder, or generalized anxiety disorder.

* * * * *